(12) United States Patent
Weese et al.

(10) Patent No.: US 7,805,182 B2
(45) Date of Patent: Sep. 28, 2010

(54) SYSTEM AND METHOD FOR THE GUIDANCE OF A CATHETER IN ELECTROPHYSIOLOGIC INTERVENTIONS

(75) Inventors: Juergen Weese, Aachen (DE); Sabine Mollus, Aachen (DE); Kai Eck, Aachen (DE); Joerg Bredno, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 545 days.

(21) Appl. No.: 11/814,821

(22) PCT Filed: Jan. 23, 2006

(86) PCT No.: PCT/IB2006/050239

§ 371 (c)(1),
(2), (4) Date: Jul. 26, 2007

(87) PCT Pub. No.: WO2006/079965

PCT Pub. Date: Aug. 3, 2006

(65) Prior Publication Data

US 2008/0139930 A1 Jun. 12, 2008

(30) Foreign Application Priority Data

Jan. 31, 2005 (EP) .................................. 05100634

(51) Int. Cl.
*A61B 5/05* (2006.01)
*A61B 6/00* (2006.01)
*A61B 5/04* (2006.01)
*A61N 1/00* (2006.01)

(52) U.S. Cl. ........................... 600/424; 607/122; 378/8; 600/509

(58) Field of Classification Search ................. 600/407, 600/424, 425, 427, 428; 607/122; 378/8
See application file for complete search history.

(56) References Cited

U.S. PATENT DOCUMENTS

| 5,345,938 | A | 9/1994 | Nishiki et al. |
| 5,391,199 | A | 2/1995 | Ben-Haim |
| 5,577,502 | A | 11/1996 | Darrow et al. |
| 5,916,163 | A | 6/1999 | Panescu et al. |
| 6,052,618 | A | 4/2000 | Dahlke et al. |
| 6,473,635 | B1 | 10/2002 | Rasche |

(Continued)

FOREIGN PATENT DOCUMENTS

JP 6054258 2/1994

*Primary Examiner*—Eric F Winakur
*Assistant Examiner*—Michael T Rozanski

(57) ABSTRACT

In a system and a method for the guidance of a catheter with an electrode in an electrophysiological procedure, sequence of images of the catheter and of a resting reference catheter is generated with an X-ray device and stored together with the associated electrographic recordings from the electrodes. A reference image may then be selected from said sequence that corresponds to a desired electrographic pattern. In a next step, the positions of the catheters are localized on the reference image. The position of the reference catheter can be identified with the position of this catheter on an actual image. Thus it is possible to determine on the actual image also a target position for the catheter that corresponds to the position of this catheter on the reference image. The target position may finally be indicated on a monitor to assist the guidance of the catheter to a desired location.

20 Claims, 1 Drawing Sheet

U.S. PATENT DOCUMENTS

| | | |
|---|---|---|
| 6,572,556 B2 | 6/2003 | Stoycos et al. |
| 6,575,901 B2 | 6/2003 | Stoycos et al. |
| 6,594,519 B2 | 7/2003 | Stoycos et al. |
| 2002/0193686 A1 | 12/2002 | Gilboa |
| 2004/0102697 A1 | 5/2004 | Evron |

SYSTEM AND METHOD FOR THE GUIDANCE OF A CATHETER IN ELECTROPHYSIOLOGIC INTERVENTIONS

FIELD OF THE INVENTION

The invention relates to an interventional system and a method for cardiovascular interventions with a catheter that records electrophysiological signals.

BACKGROUND OF THE INVENTION

There are increasingly more electrophysiological (EP) procedures carried out on cardiovascular X-ray systems. These procedures require a long time with a typical duration of several hours and an associated large patient X-ray dose. It is, therefore, important to provide functionality to the X-ray system which facilitates system usage, shortens the time for performing the procedure, and reduces X-ray dose.

One particular example of an EP procedure is the minimally invasive treatment of tachycardias, i.e. abnormally rapid rhythms of the heart. Multiple fibers run through the heart muscles that are responsible for the propagation of electrophysiological signals. The presence of arrhythmogenic tissue or abnormal pathways bypassing the normal conducting fibers can cause tachycardias. During a minimally invasive treatment, the locations of arrhythmogenic tissue or abnormal pathways are determined by mapping the electrophysiological excitation signals. E.g., the delay of an excitation signal from a reference to the current position or irregular excitation sources are depicted for one or more heart cavities. After signal mapping, an ablation catheter is directed to the identified target sites and alternating current, cryotherapy, or other means are applied to locally destroy the cardiac tissue that causes the tachycardias. It is characteristic for this procedure that X-ray fluoroscopy is used to provide (rough) spatial positions of the catheter with respect to the heart anatomy while the electrophysiological signals provide the actual diagnostic information.

At various points during such an intervention, it is required to direct the catheter to a position with a characteristic, previously observed EP signal. For that purpose, the EP signals can be recorded together with related fluoroscopy sequences, and at a later point in time a combined EP-X-ray sequence can be selected, regained and displayed (cf. e.g. U.S. Pat. No. 6,572,556 B2). The navigation of the catheter to the location with a desired EP signal remains however a rather difficult and lengthy procedure.

SUMMARY OF THE INVENTION

Based on this situation it was an object of the present invention to provide means for a facilitated guidance of a catheter that records electrophysiological signals during an intervention.

According to its first aspect, an interventional system for cardiovascular interventions has the following components:

A catheter with at least one electrode that can sense electrophysiological signals from tissue (e.g. the heart muscle). If the catheter has more than one electrode (like a so-called "Basket-catheter"), then a multitude of signals will be recorded at a multitude of positions, but still, a fixed mapping of positions to recorded ECG signals is provided.

An electrographic device that is coupled to the aforementioned electrode of the catheter and that is adapted to measure electrophysiological potentials sensed by said electrode. Electrographic devices of this kind are well known in the state of the art (e.g. for electrocardiography, electromyography, or electroencephalography) and will therefore not be described in more detail here. By monitoring the recorded electrophysiological potentials, it is possible to diagnose the tissue at the position of the electrode.

An imaging device for generating images of a region where the intervention takes place (called "interventional region" in the following). The imaging device may for example be an X-ray device, a magnetic resonance imaging (MRI) device, or an ultrasound device. On the images generated with the device, the catheter shall be visible such that it can be navigated through all heart cavities with the help of the images.

A data processing unit that may for example be realized by a microcomputer with associated components like central processing unit (CPU), memory (RAM, ROM, hard disc etc.), I/O interfaces and with appropriate software. The data processing system is coupled to the electrographic device and the imaging device to receive signals from these components and, optionally, also to control them. Moreover, it is adapted to perform the following steps:

a) The storage of a sequence of images of the catheter in the interventional region that were are generated by the imaging device, wherein each image is stored together with an associated, typically synchronous electrographic recording (which is by definition recorded during the generation of the image). The recordings then reflect the electrophysiological conditions at the position where the electrode of the catheter resides on the corresponding image or image sequence.

b) The generation of an image of the catheter within the interventional region. During an intervention, said image is typically a (fluoroscopic) live image and will therefore be called the "actual image" in the following. This shall however not be understood as a limitation with respect to the time at which said image is generated. Moreover, electrographic potentials may optionally be recorded parallel to the generation of the actual image, similar to the procedure of step a).

c) The selection of a "reference image" from the stored sequence of step a), wherein said reference image shall belong to a desired electrographic pattern (recording). The desired electrographic pattern is usually predetermined by the physician and typically represents tissue with a malfunction.

d) The localization of the position of the catheter on the reference image, wherein the "position" includes one or more points (e.g. derming a curved path) and wherein said localization may be achieved by any suitable method known from digital image processing. Moreover, a "target position" for the catheter is determined on the actual image, wherein said target position corresponds to the localized position of the catheter on the reference image. In other words, the localized position of the catheter on the reference image is registered with the corresponding position on the actual image. Said registration is preferably based on the fixed landmarks of the imaged body part, i.e. anatomical positions on the reference image are mapped onto the identical anatomical positions on the actual image.

An interventional system of the aforementioned kind is very helpful for the navigation of a catheter during electrophysiological procedures, because the determination of the target position on a live image helps to guide the catheter to the desired tissue showing a characteristic electrographic pattern. It is no longer necessary to find said tissue in a lengthy iterative procedure of advancing the catheter stepwise while comparing the recorded electrographic signals with the desired ones. Thus the duration of the intervention can be reduced, which means less stress and X-ray exposure for the patient and the medical personnel.

The determination of a target position in step d) can be achieved by different methods known from digital image processing. The reference image and the actual image may for instance be registered based on their content, e.g. by finding the superposition of the images with maximized local similarity. According to a preferred embodiment, the determination is based on the localization of at least one characteristic point of the body part shown on the reference image and the actual image. A characteristic point may for example be an anatomical landmark like the apex of the heart or distinguished positions in the atria like the pulmonary veins.

In another embodiment, the interventional system comprises a reference instrument, wherein the position of this instrument is known for each image of the stored sequence and for the actual image relative to the other images. Thus the reference instrument may be considered as a mark that allows an object-based registration of the images of the sequence and the actual image. The reference instrument may particularly be a second or "reference" catheter. A reference catheter with a reference electrode is generally required in electrophysiological measurements and typically kept at the same anatomical position during an intervention. If the reference catheter is relocated during the intervention, this does not prevent its use as mark on the images as long as the extent of said relocation is know such that it can be taken into account.

The interventional system preferably also comprises a display unit, for example a monitor, for displaying the actual image together with an indication of the determined target position. Thus the physician can direct the catheter to the target position under direct visual control.

The localization of the catheter (or its electrode) and/or of the reference instrument (if present) on the reference image can be facilitated if it is identified on one image of the images of the sequence and then tracked in the other images of the sequence. The localization on any image may thus be based on the already know locations on the (with respect to the temporal order of the image sequence) previous/following image. The identification of the catheter or the reference instrument on a first image may be interactively achieved with the help of a user. The human interaction is particularly helpful for distinguishing the (interventional) catheter from a reference catheter, because they both may look identical or very similar to each other on the images. In this case the identification provided by the user can be propagated to all images by the mentioned tracking.

In a further development of the investigation system, a reference image is selected that corresponds to the same heart phase as the actual image (while of course simultaneously belonging to the desired electrophysiological pattern). The heart phase that corresponds to an image can readily be determined because electrographic signals are recorded parallel to the image generation. By the selection of an image with a similar heart phase as the actual image, movements and/or deformations of the interventional region due to heart beat can be reduced a minimum.

The system may furthermore be adapted to compensate the effect that respiration motion has on the catheter and/or on a reference instrument in the sequence of images and in the actual image. Respiration motion may particularly be compensated based on the a-priorily extracted motion of catheter positions due to respiration and a continuous determination of the depth of respiration from acquired images or external respiration sensors.

To achieve an optimal accuracy, the aforementioned approaches are preferably combined. Thus the system can display the position of a (reference) catheter after compensation of heart beat and respiration motion, wherein heart beat motion is compensated by continuously updating the selection of the reference image such that it corresponds to the heart phase of the actual image, which is identified by the synchronously acquired ECG. The compensation of both kinds of motions is particularly important for the accurate navigation and repositioning of a catheter at a previously determined position.

In another variant, the catheter and/or the reference instrument are provided with markers that allow the determination of their spatial position. Said markers may for example be X-ray dense materials which can readily be located on X-ray images. Preferably the markers belong to a non-line-of-sight localization system, for example as Hall sensors that measure the magnitude and direction of an inhomogeneous external magnetic field. Suitable markers of such systems are known in the state of the art and will therefore not be described in more detail here.

The invention further comprises a method for the guidance of a catheter with an electrode in an interventional region during a cardiovascular intervention. In one embodiment, the method includes the following steps:
a) generating and storing a sequence of images of the catheter in the interventional region together with associated electrographic recordings;
b) generating an actual image of the catheter in the interventional region;
c) selecting a reference image from the stored sequence of images that belongs to a desired electrographic pattern;
d) locating the position of the catheter on the reference image and determining a corresponding target position on the actual image.

The method comprises in general form the steps that can be executed with an investigation system of the kind described above. Therefore, reference is made to the preceding description for more information on the details, advantages and improvements of that method.

According to a preferred embodiment, the method comprises a reference instrument, particularly a reference catheter, that is disposed in the interventional region, wherein the relative position of said instrument is known in all images. This position can therefore be used as a mark for the registration of the reference image and the actual image.

These and other aspects of the invention will be apparent from and elucidated with reference to the embodiment(s) described hereinafter.

BRIEF DESCRIPTION OF THE DRAWINGS

In the following, an embodiment of the invention is described by way of example.

The FIGURE schematically illustrates an embodiment of an interventional system.

DESCRIPTION OF PREFERRED EMBODIMENTS

Figure 1:
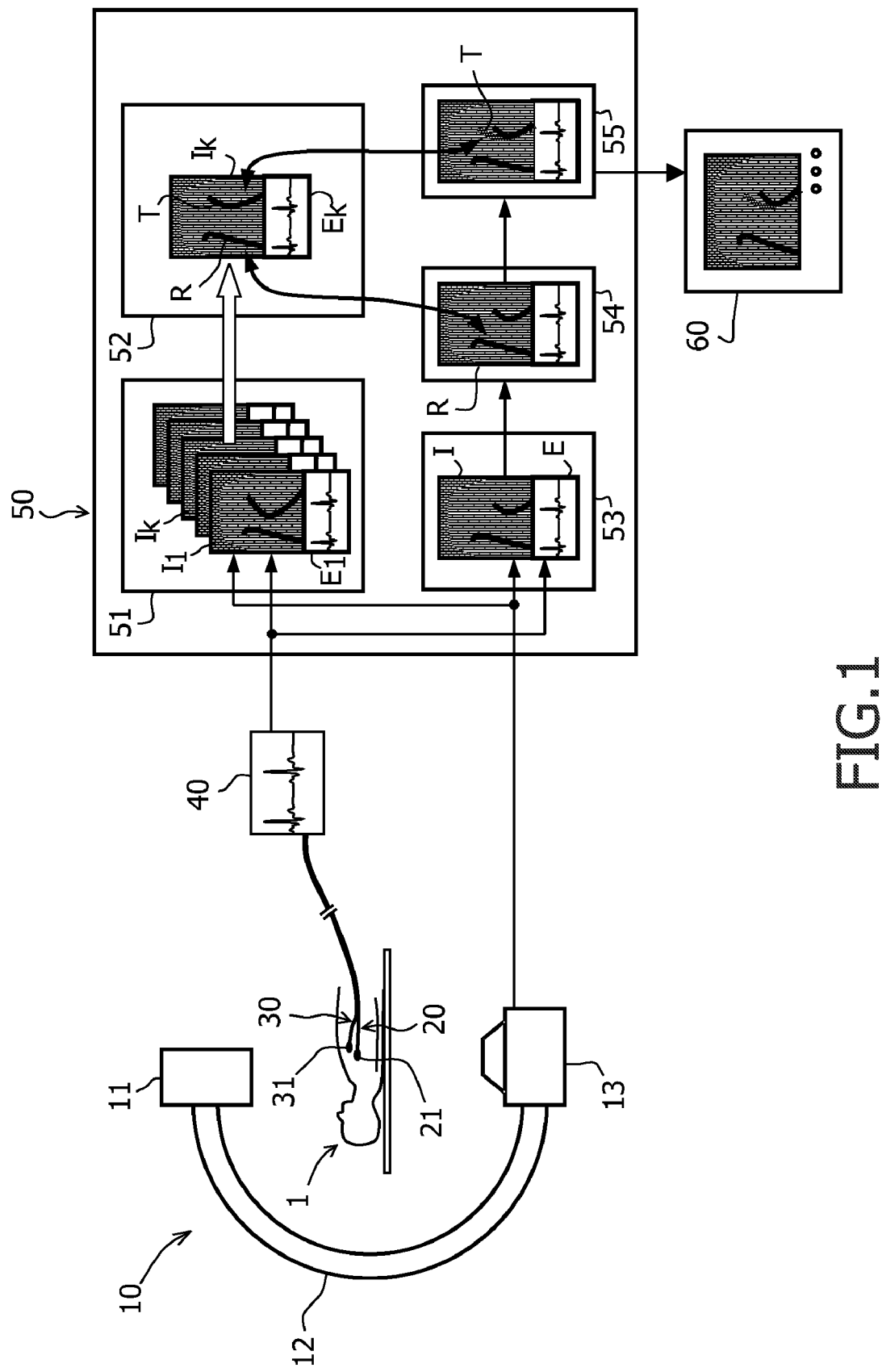

On the left side of the FIGURE, a rotational X-ray device 10 is depicted that consists of an X-ray tube 13 and an X-ray detector 11 which are connected by a C-arm 12. The X-ray device 10 allows the generation of X-ray projections from different directions of a patient 1 lying on a table in the centre of the device. Instead of an X-ray device, other imaging devices could be used as well.

The FIGURE further shows a catheter 20 that is advanced through the vessel system of the patient 1 into the heart. An electrode 21 at the tip of the catheter is coupled to an electrocardiographic device 40 for recording electrophysiological potentials of the tissue contacting the electrode 21. For the electrophysiological measurements, a second or "reference" catheter 30 is present and connected to the electrographic device 40, too, wherein said catheter 30 and its reference electrode 31 usually rest at a constant anatomical position during the whole intervention.

A typical application of the system is the minimally invasive treatment of a tachycardia caused by arrhythmogenic tissue or abnormal pathways in the heart of the patient 1. During such an intervention, the electrode 21 of the catheter 20 must be brought to the same anatomical position several times, wherein the correct positioning is diagnosed by the recorded electrophysiological potential. The depicted system is particularly adapted to assist the physician in this repositioning of the catheter 20 as will be described in more detail in the following.

The X-ray device 10 and the electrographic device 40 are connected to a data processing unit 50, e.g. a workstation. The FIGURE illustrates different modules of said data processing unit 50 which are primarily realized by software.

In a first module 51, a sequence of images $I_1, \ldots I_k, \ldots$ generated by the X-ray device 10 is stored together with electrographic recordings $E_1, \ldots E_k, \ldots$ from the electrode 21 that were recorded at the time the images were generated. It should be noted that the electrographic recordings $E_1, \ldots E_k, \ldots$ typically last several seconds or even minutes, while the generation of the X-ray images is accomplished much faster. The electrographic recordings represent the electrophysiological signals produced by the tissue at the position of the electrode 21 of the catheter 20 in the generated image.

In a second module 53, an actual or live (fluoroscopic) image I of the interventional region is maintained together with a corresponding electrophysiological recording E measured by the electrodes 21, 31 of the device 40. Said actual image I represents the current position of the catheter 20 during an intervention.

As was already mentioned above, a typical task during an electrophysiological procedure is to redirect the catheter 20 (or, more precisely, its electrode 21) to a previously taken position that is characterized by a certain electrographic signal pattern. To assist this task, an electrographic recording $E_k$ similar to this desired pattern is searched in module 51, and the associated image $I_k$ of the image sequence is selected and transferred to a module 52 as the so-called "reference image" $I_k$.

On the reference image $I_k$, the image or "target position" T of the catheter 20 and the image or "reference position" R of the reference catheter 30 can be determined by procedures known in digital imaging processing.

In a similar step, the position R' of the reference catheter 30 can be determined on the actual image I in module 54. As the reference catheter 30 has a fixed position in the heart and does not move relative to the heart, it marks the same anatomical position (or connected path of positions) in both the reference image $I_k$ and the actual image I. This makes it possible to match the images of the catheter 30 (e.g. using grey-level based registration or a geometric matching of detected and segmented catheters) and thus to register both images I and $I_k$, i.e. to bijectively map corresponding (anatomical) points of both images onto each other. Based on this registration, the target position T previously localized in the reference image $I_k$ can be transferred to the corresponding target position T' in the actual image I as symbolized in module 55.

As a last step, the actual image I can be displayed on a monitor 60 together with an indication (e.g. a colored representation and/or an arrow pointing to the tip of the catheter) of the target position T the catheter 20 has to be moved to.

The identification of the reference catheter 30 and the (interventional) catheter 20 in the images can be done manually by indicating a point on respective catheters in the reference image $I_k$. Alternatively, the reference and the interventional catheter may be indicated once in a fluoroscopy image at the very beginning of the procedure and respective information can be propagated to subsequent frames by tracking the catheters. A-priori information of the position of the reference catheter or markers identifiable by computer vision (e.g. due to their number and/or mutual distance) can also be used for this identification.

Catheter tracking can also help if the reference catheter would be moved at some point in time during the intervention. In that case, the interventional catheter 20 can be used as reference to estimate the movement of the reference catheter 30. Respective transformation can then be taken into account within the overlay.

Further extensions of the procedure comprise the use of ECG information to select images of the sequence $I_1, \ldots I_k, \ldots$ and an actual fluoroscopy sequence with corresponding heart contraction phase such that the navigational guidance is presented with a compensation of the sometimes strong heart beat motion. Similarly, an analysis of the cyclic respiration motion can be taken into account to improve accuracy. The depth of respiration can be determined from acquired images using digital image processing or by external sensors, e.g. a belt with stretch sensors around the patient's abdomen or lower chest. This allows to separately determine the motion of catheters due to respiration and heartbeat. Furthermore, position information from non-line-of-sight localizers attached to respective catheters may be used within matching and the subsequent overlay, for instance to add depth information or to replace computer vision algorithms with direct position measurements.

The described system facilitates regaining of a catheter position corresponding to a specific EP signal during EP procedures. Since the physician is better supported, the specific intervention can be performed faster with less X-ray exposure for patient and staff.

Finally it is pointed out that in the present application the term "comprising" does not exclude other elements or steps, that "a" or "an" does not exclude a plurality, and that a single processor or other unit may fulfill the functions of several means. The invention resides in each and every novel characteristic feature and each and every combination of characteristic features. Moreover, reference signs in the claims shall not be construed as limiting their scope.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. An interventional system for cardiovascular interventions, comprising
   a catheter with an electrode;
   an electrographic device that is coupled to the electrode of the catheter which generates electrophysiological maps from electrophysiological excitation patterns measured at locations in an interventional region which come into electrical communication with the electrode;
   an imaging device which acquires images of the interventional region;

a data processing unit coupled to the imaging device and the electrographic device configured to perform the following steps:

a) storing a sequence of pre-operatively acquired images ($I_1, \ldots I_k, \ldots$) of the catheter in the interventional region, each image being stored in association with a corresponding electrophysiological map ($E_1, \ldots E_k, \ldots$) measured concurrently during its acquisition;

b) acquiring an actual image (I) of the catheter in the interventional region during a live intervention;

c) selecting a reference image ($I_k$) from the stored sequence of pre-operative images ($I_1, \ldots I_k, \ldots$) according to a degree of similarity between the associated electrophysiological map and a desired electrophysiological pattern ($E_k$);

d) locating a reference position (T) of a reference probe of the catheter in the selected reference image ($I_k$) and determining a corresponding target position (T') in the actual image (I).

2. The system according to claim 1, wherein the determination in step d) is based on the localization of at least one characteristic point (R, R') of the imaged object in the reference image ($I_k$) and the actual image (I).

3. The system according to claim 1, wherein the reference probe is disposed in the interventional region such that the position (T) of the reference probe is known in all of the stored sequence of pre-operative images ($I_1, \ldots I_k, \ldots$) and in the actual image (I).

4. The system according to claim 1, further including:
a display unit for displaying the actual image (I) together with an indication of the determined target position (T').

5. The system according to claim 1, wherein the imaging device is an X-ray device.

6. The system according to claim 1, wherein the reference probe is identified on at least one of the images ($I_1, \ldots I_k, \ldots$) of the pre-operative sequence and tracked in the other images.

7. The system according to claim 1, wherein the reference image ($I_k$) is selected such that it corresponds to a heart phase indicated by the electrographic device when the actual image (I) is generated.

8. The system according to claim 1, wherein the data processing unit is configured to compensate for the effect of respiration motion on the catheter in the sequence of pre-operative images ($I_1, \ldots I_k, \ldots$) and the actual image (I).

9. The system according to claim 8, further including:
a respiration sensor which senses the respirator motion.

10. The system according to claim 1, wherein the catheter and/or the reference probe are provided with markers that are imaged by the imaging device such that their spatial position is determined in the sequence of pre-operative images ($I_1, \ldots I_k, \ldots$) and the actual image (I).

11. A method for the guidance of a catheter with an electrode which generates electrophysiological maps from electrophysiological excitation patterns measured at locations in an interventional region which come into electrical communication with the electrode, comprising:

acquiring and storing a sequence of pre-operative images ($I_1, \ldots I_k, \ldots$) of the catheter in the interventional region, each image being stored in association with a corresponding electrophysiological map ($E_1, \ldots E_k, \ldots$) measured concurrently during its acquisition;

acquiring an actual image (I) of the catheter in the interventional region during an intervention;

selecting a reference image ($I_k$) from the stored sequence of pre-operative images ($I_1, \ldots I_k, \ldots$) based on a degree of similarity of a desired electrophysiological pattern ($E_k$) to the electrophysiological map associated with one of the pre-operative images;

locating a reference position (T) of a reference probe of the catheter in the reference image ($I_k$) and determining a corresponding target position (T') in the actual image (I).

12. The method according to claim 11, wherein the reference probe is disposed in the interventional region during the acquiring of the pre-operative and actual images such that the position (T) of the reference probe is known in all images.

13. A non-transitory computer readable medium carrying a computer program which controls on or more processors to perform the method according to claim 11.

14. An interventional system for cardiovascular interventions, comprising
a catheter with an electrode at an operating end;
an electrographic device coupled to the electrode of the catheter which measures electrophysiological maps ($E_1, \ldots E_k, \ldots$) from electrophysiological excitation patterns of tissue at locations in an interventional region which come into electrical communication with the electrode;
an imaging device which acquires a series of pre-operative images ($I_1, I_k, \ldots$) and at least one interventional image (I), the catheter being imaged with the tissue in the interventional region;
a data processor coupled to the imaging device and the electrographic device and programmed to:

a) store the sequence of pre-operative images ($I_1, \ldots I_k, \ldots$) of the catheter in the interventional region, each pre-operative image being stored with one of the associated electrophysiological maps ($E_1, \ldots E_k, \ldots$) measured concurrently with each pre-operative image;

b) compare an electrophysiological map corresponding to a current interventional image with the stored electrophysiological maps; and c) select a reference image ($I_k$), the reference image being one of the pre-operative images stored in association with an electrophysiological map most similar to the electrophysiological map of the current interventional image.

15. The interventional system according to claim 14, wherein the data processor is further programmed to:

d) determine a reference target position (T) for a location of the catheter electrode in the reference image ($I_k$); and e) transform the reference target position (T) to a corresponding interventional target position (T') in the current interventional image (I).

16. The interventional system according to claim 15, wherein the data processor is further programmed to:
reposition the catheter electrode from a current location to the interventional target position (T'); and
apply ablation therapy to cardiac tissue at the interventional target position (T').

17. The interventional system according to claim 14, further including:
a reference probe having a fixed position relative to the interventional region from which a characteristic point (R,R') can be determined in both of the pre-operative images ($I_1, \ldots I_k, \ldots$) and the current interventional image (I); and
wherein the data processor is further programmed to transform the reference target position (T) to the corresponding interventional target position (T') using the reference position (R,R').

18. The interventional system according to claim 14, wherein the imaging system includes an X-ray imaging system which acquires X-ray images as the pre-operative image ($I_1, \ldots I_k, \ldots$) and a fluoroscopic image as the current interventional image (I).

19. The interventional system according to claim 14, wherein a cardiac phase of the selected reference image ($I_k$) corresponds to a heart phase of the current interventional image (I).

20. The interventional system according to claim 19, wherein a respiratory phase of the reference image ($I_k$) is transformed to a respiratory phase of the current interventional image (I).

* * * * *